United States Patent [19]

Lauffer

[11] 4,291,271
[45] Sep. 22, 1981

[54] METHOD FOR DETERMINING PORE SIZE DISTRIBUTION AND FLUID DISTRIBUTION IN POROUS MEDIA

[75] Inventor: Donald E. Lauffer, Bartlesville, Okla.
[73] Assignee: Phillips Petroleum Company, Bartlesville, Okla.
[21] Appl. No.: 90,180
[22] Filed: Nov. 1, 1979
[51] Int. Cl.³ .............................................. G01N 27/00
[52] U.S. Cl. .................................... 324/307; 324/303
[58] Field of Search ............... 324/303, 307, 311, 313, 324/314

[56] References Cited

U.S. PATENT DOCUMENTS

| | | |
|---|---|---|
| 2,705,790 | 4/1955 | Hahn . |
| 2,913,658 | 11/1959 | Burdine . |
| 3,213,355 | 10/1965 | Woessner . |
| 3,275,931 | 9/1966 | Collins . |
| 4,051,429 | 9/1977 | Imanari .............................. 324/311 |
| 4,068,161 | 1/1978 | Ernst .................................. 324/311 |
| 4,219,775 | 8/1980 | Bozanic ............................. 324/313 |

*Primary Examiner*—Michael J. Tokar

[57] ABSTRACT

The pore size distribution and the distribution of fluid in a porous media, such as a reservoir rock formation, is determined by nuclear magnetic resonance spectrometry technique. A sequence of three radio frequency pulses is applied to a sample which is placed in a large static magnetic field. The resultant spin echo is measured and is utilized to determine the pore size distribution in the porous medium. If water is present in the sample, the sample is doped so as to substantially eliminate the nuclear magnetic resonance response of the hydrogen in water. The technique can be utilized to distinguish between hydrocarbon filled and water filled pores in the sample thus providing information concerning the fluid distribution in the sample.

21 Claims, 7 Drawing Figures

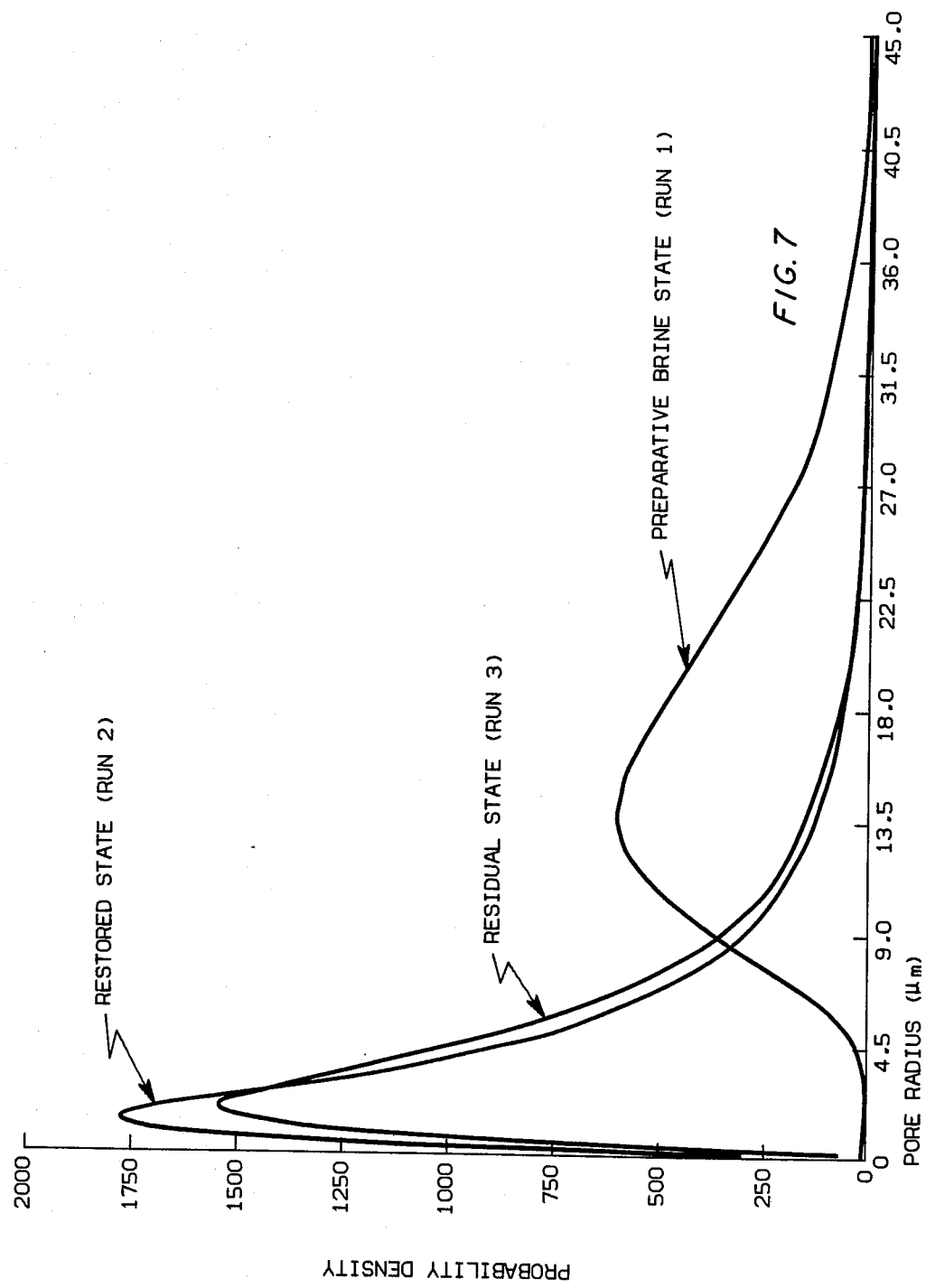

METHOD FOR DETERMINING PORE SIZE DISTRIBUTION AND FLUID DISTRIBUTION IN POROUS MEDIA

This invention relates to a method for determining the pore size distribution in porous rock. In another aspect this invention relates to a method for determining the size distribution of pores containing hydrocarbons in porous rock.

A knowledge of the pore size distribution and which pores contain hydrocarbons is useful to reservoir engineers in designing means for efficiently recovering crude oil from such reservoirs. This knowledge is of particular importance in tertiary oil recovery in the selection of appropriate flooding materials to recover the crude oil remaining after primary and secondary recovery techniques have either been employed or are considered unsuitable.

It is thus an object of this invention to provide a method for determining the pore size distribution in porous rock. It is another object of this invention to provide a method for determining the size distribution of pores containing hydrocarbons in porous rock.

In accordance with the present invention, a method is provided in which a jacketed sample of a porous media which is substantially saturated with a fluid or mixture of fluids is positioned in the static magnetic field ($H_o$) of a nuclear magnetic resonance (NMR) spectrometer. The NMR spectrometer is modified to provide means for imposing a magnetic field gradient (G) and an alternating magnetic field ($H_1$) on the sample.

Since an electric charge is associated with a spinning atomic nucleus, this spinning nucleus generates a magnetic field and behaves similarly to a tiny magnet of magnetic moment $\mu$. When the nuclear magnet is placed in the static magnetic field ($H_o$), the axis of the nuclear magnet will tend to orient with the applied magnetic field. However, since the nucleus has angular momentum, the net effect is that the rotational axis precesses around the applied magnetic field. The frequency of precession which is characteristic of particular type of nucleus is called the Larmor frequency and is equal to the product of the gyromagnetic ratio ($\gamma$) and the magnetic field strength of the static magnetic field ($H_o$). If a sinusoidal radio frequency (RF) magnetic field $H_1$ is applied normal to the static field $H_o$ and is equal to the Larmor frequency of the nucleus, the well known condition called "resonance" results and a net absorption of magnetic energy is observed on the detector of the NMR spectrometer.

After the nuclear magnets associated with the fluid in the sample of a porous media have oriented with the static magnetic field ($H_o$), an initial radio frequency pulse is introduced into the sample at an amplitude and for a time duration sufficient to rotate the precessing nuclear magnet by approximately 90°. Relaxation caused by spin-spin interactions will occur after the first pulse is applied. A second radio frequency pulse is then applied to further rotate the precessing nuclear magnet another approximately 90°. Further relaxation will occur which is primarily due to spin-lattice interactions. After a period of time sufficiently long to allow appreciable diffusional interaction with the pore walls, a third radio frequency pulse is applied in order to rotate the precessing nuclear magnet through another approximately 90°. Following the application of the third radio frequency pulse, the magnetization is refocused which produces what will be referred to as the stimulated spin echo. The amplitude of the stimulated spin echo signal is reduced from that of the original magnetization by the relaxation which occurred due to diffusion, spin-spin interactions and spin-lattice interactions.

The reduction of the amplitude of the spin echo signal due to diffusional relaxation provides the basis for calculating the pore size distribution. The amplitude of the stimulated spin echo is given by the expression:

$$S(\tau_1, \tau_2, G, \mu, \sigma) = \frac{\int_0^\infty R^3 M(R, G, \tau_1, \delta) P(R, \mu, \sigma) dR}{\int_0^\infty R^3 P(R, \mu, \sigma) dR} \quad (I)$$

wherein
$\tau_1$ = Time from first to second pulse.
$\tau_2$ = Time from first to third pulse.
G = Magnetic field gradient.
$\mu$ = Mean of lognormal distribution of pore radii.
$\sigma$ = Standard deviation of lognormal distribution of pore radii.
R = Pore radius.
$\delta = \tau_2/\tau_1$ In the above expression $M(R, G, \tau, \delta)$ is the maximum amplitude of the stimulated spin echo and $P(R, \mu, \sigma)$ is a lognormal distribution which is chosen to describe the distribution of pore radii. For a given diffusion time, $\tau_2 + \tau_1$, values of $\mu$ and $\sigma$ are calculated by optimizing the least square fit of Equation I to the experimental spin echo data.

If the sample is saturated with a brine solution, then the values of $\mu$ and $\sigma$ provide an indication of the pore size distribution of the core sample and the standard deviation of the pore size distribution in the core sample. If the sample is filled with a hydrocarbon containing fluid and a doped water solution, then the values of $\mu$ and $\sigma$ provide an indication of the size distribution of the pores which contain the hydrocarbon containing fluid. The information concerning the pore size distribution of all of the pores in the core sample and the pore size distribution of the pores containing the hydrocarbon containing fluid may be utilized by a reservoir engineer to select an appropriate flooding material to recover the crude oil remaining in the rock formation.

Other objects and advantages of the invention will be apparent from the foregoing brief description of the invention and the appended claims as well as the detailed description of the drawings in which:

FIG. 7 is a graphical illustration of the data obtained in the example.

Figure 1:
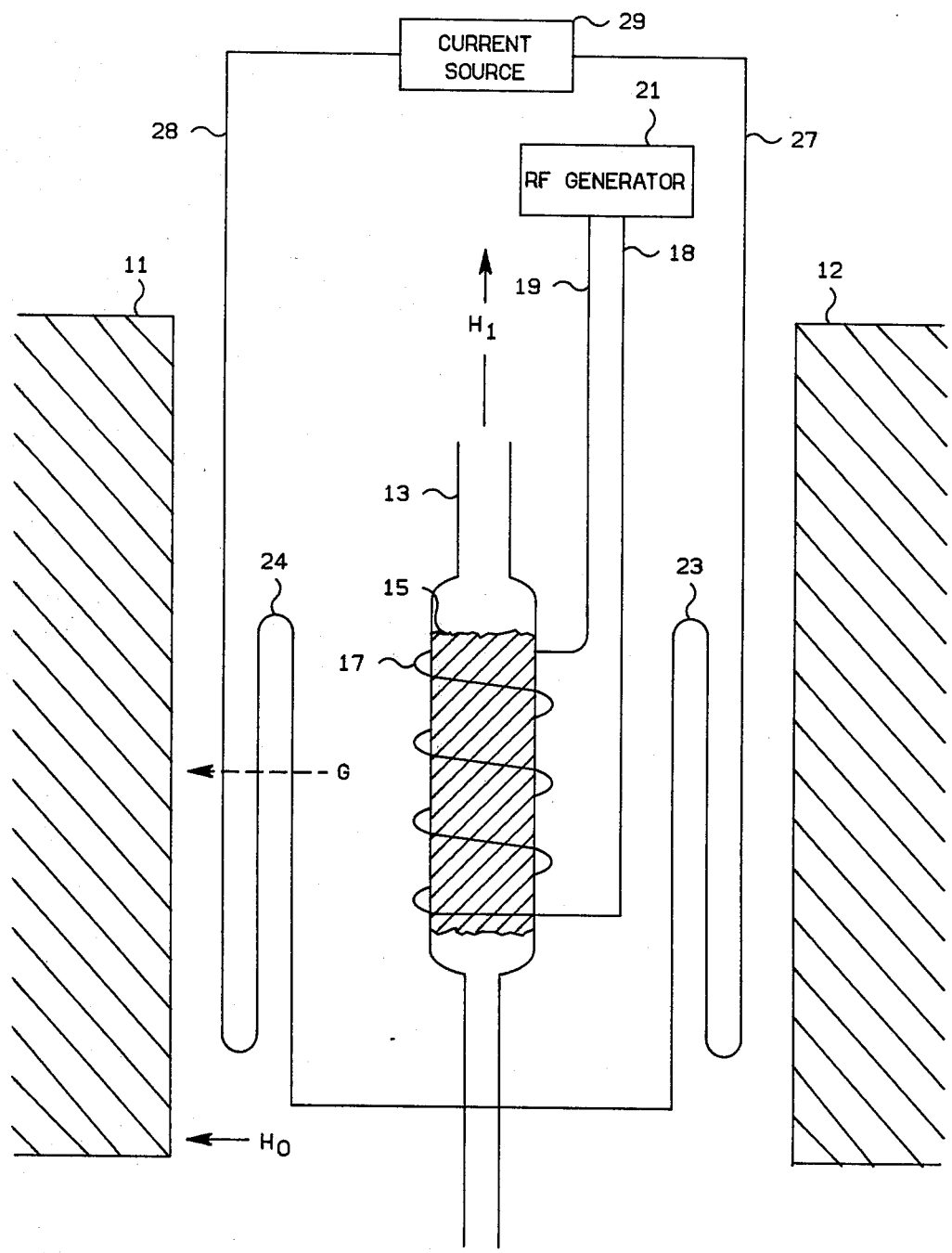
FIG. 1 is a simplified diagramatic illustration of the apparatus for subjecting the sample to both a static magnetic field and an alternating magnetic field.
Figure 2:
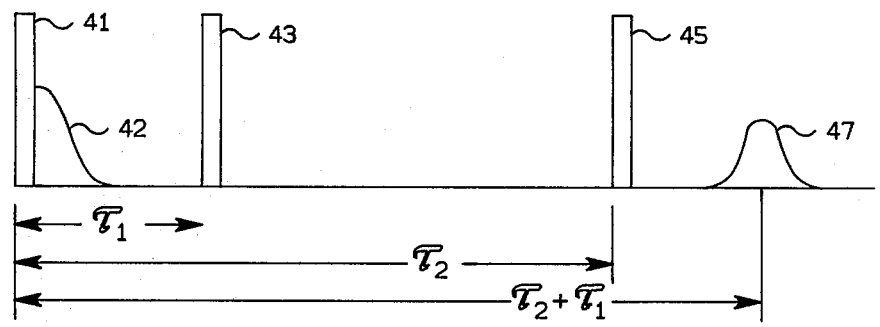
FIG. 2 is a timing diagram for the application of the radio frequency pulses.

Referring now to FIG. 1, a static magnetic field of magnitude $H_o$ is produced by an electromagnet with opposing poles 11 and 12. A sample holder 13 containing the desired sample 15 in the power portion thereof is positioned in the air gap between the opposing poles of the electromagnet. A wire coil 17 encompasses the lower portion of sample holder 13 containing the sample 15. Leads 18 and 19 connect coil 17 to a source 21 of alternating current of frequency which can be varied but is normally set at a particular value. Application of alternating current through coil 17 produces alternating magnetic field pulses $H_1$ which are perpendicular to static magnetic field $H_o$. Secondary field coils 23 and 24 (opposing Helmholtz coils) attached through leads 27 and 28 to a current source 29 produce a constant magnetic field gradient G superpositioned on $H_o$.

The apparatus illustrated in FIG. 1 is essentially a modified NMR spectrometer. The NMR spectrometer to be modified is selected from well known broad band NMR spectrometers, a number of which are commercially available. The NMR spectrometer is coupled to a high speed digitizer. The magnet of the NMR spectrometer which is represented by the electromagnet having opposing poles 11 and 12 is of reasonably high resolution. The gradient is at least one order of magnitude less than the imposed gradient G. The gap of the magnet is preferably greater than 4 centimeters in order for the sample 15, the coil 17 and the secondary field coils 23 and 24 to be inserted between the poles 11 and 12 of the magnet.

The stimulated spin echo experiment which is performed utilizing the apparatus illustrated in FIG. 1, will be described with reference to FIGS. 2–6. The stimulated spin echo experiment is most easily described by using a reference frame which rotates about the direction of $H_o$ at a frequency equal to the Larmor frequency. By convention, the Z axis and the X axis of the rotating reference frame are defined to coincide with $H_o$ and $H_1$, respectively. FIGS. 3–6 are highly simplified diagrams representing the behavior of the precessing axis of the nuclear magnet relative to the rotating reference frame during the stimulated spin echo experiment. Relaxation of the NMR signal is due to spin-spin and spin-lattice interactions, as well as diffusion. The term spin-spin interactions is utilized to refer to interactions between the nuclear magnets oriented perpendicular to the static magnetic field. The term spin-lattice interactions is utilized to refer to interactions between the nuclear magnets oriented parallel to the static magnetic field.

Figure 3:
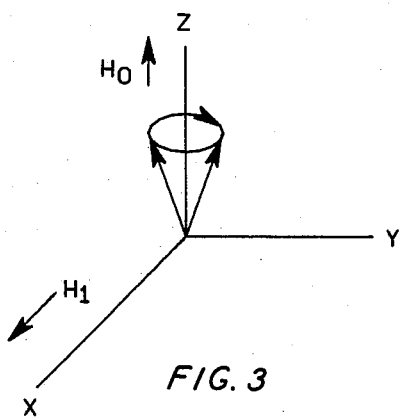
FIGS. 3–6 are diagramatic illustrations of the precessing nuclear magnet.
Figure 4:
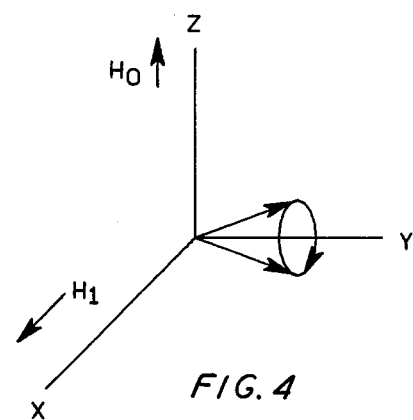

FIG. 3 represents the precession of the nuclear magnet in the static magnetic field $H_o$ prior to the application of any radio frequency pulse. The axis of the nuclear magnet will tend to orient with the applied magnetic field $H_o$ as is illustrated in FIG. 3. An initial radio frequency pulse 41 (FIG. 2) is then introduced through coil 17 at an amplitude and for a duration sufficient to rotate the precessing nuclear magnets by approximately 90° to generally the Y axis. Preferably the rotation of the precessing nuclear magnets is as close as possible to 90°. Rotation within ±5° of 90° is typical. The thus rotated precessing nuclear magnet is illustrated in FIG. 4. Relaxation which occurs after the first pulse is dominated by spin-spin interactions since spin-spin interactions predominate for porous rock samples when the magnetization is perpendicular to the magnetic field $H_o$. After a sufficiently long time during the interval $\tau_1$ (FIG. 2), the NMR signal which is represented as 42 will become unobservable because of angular dephasing caused by the fact that not all of the nuclear magnets will be rotating at a frequency equal to the Larmor frequency.

Figure 5:
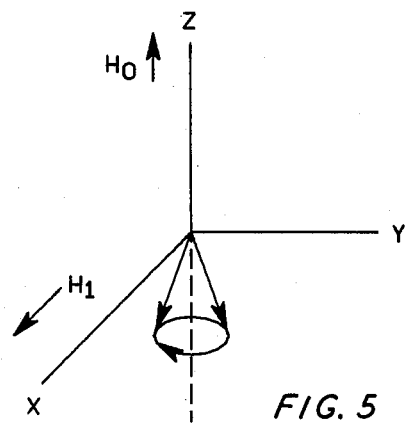
Figure 6:
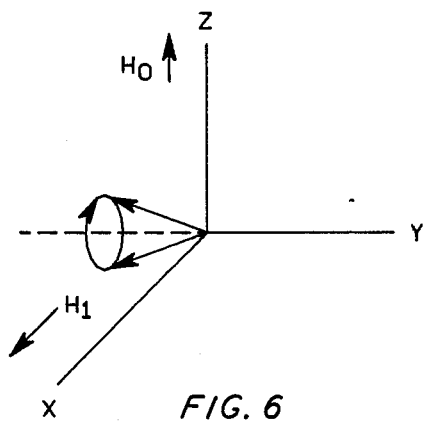

After a time period which is represented as $\tau_1$ has elapsed, a second radio frequency pulse 43 is applied to further rotate the precessing nuclear magnets another approximately 90° to generally the X-Z axis pulse as is illustrated in FIG. 5. Relaxation of the signal which occurs after the second pulse is primarily due to spin-lattice interactions since these interactions are predominant when the magnetization is parallel or anti-parallel to the applied magnetic field $H_o$.

After a period of time sufficiently long to allow an appreciable diffusional interaction with the pore walls, a third radio frequency pulse 45 (FIG. 2) is applied in order to rotate the precessing magnets through another approximately 90° to generally the X-Y plane (FIG. 6) in which position again spin-spin relaxation is predominant. Following the application of the third pulse, the magnetization is refocused along generally the negative Y axis, thus producing the observed stimulated spin echo 47. The amplitude of the stimulated spin-echo 47 is reduced from that of the original magnetization 42 by the relaxation which occurred due to diffusion, spin-spin interactions and spin-lattice interactions.

The amplitude of the spin echo signal 47 is utilized in conjunction with Equation I to derive values for the mean and standard deviation of the pore size distribution for the sample. For Equation I, a spherical model of a pore was chosen although cylindrical, rectangular or other models could have been chosen if desired. A log-normal distribution for the pores in the sample was chosen because in naturally occuring formations, a log-normal distribution is typical. $\tau_1$ and $\tau_2$ of Equation I will be known. The gradient G is varied and a plurality of spin echo signals are measured. The amplitude of the plurality of stimulated spin echo signals is plotted as function of the magnetic field gradient G. A nonlinear optimization program is then utilized to calculate values of $\mu$ and $\sigma$ which will enable Equation I to fit the curve generated from the experimental data. Depending on the fluid saturation in the core sample, the values of $\mu$ and $\sigma$ will give either the pore size distribution for the sample or the pore size distribution for crude oil containing pores. The specific method steps required to obtain these pore size distributions will be described more fully hereinafter.

In order to determine the pore size distribution of porous rock samples, it is necessary to saturate the desired sample with a liquid which exhibits a response in the NMR spectrometer, e.g., water or an organic liquid for which proton resonance is observed. The diffusion of these species within the pores of the rock as a function of time results in the relaxation of the NMR signal and the corresponding decrease in the signal amplitude of the spin echo from which the pore size distribution is determined.

The porous rock sample to be studied by means of this invention is generally cylindrical in shape with a length of about 3–5 cm and a diameter of 1–2 cm. The size of the porous rock sample is not critical to this invention. The size is important only in that it should be sufficiently small to fit conveniently into the cavity of the instrument and large enough to give a representative sample and to be easily prepared with sufficient structural strength to be easily handled.

It is desirable to encase the porous rock sample in a tightly-fitting film in order to prevent the liquid contained therein from draining or from evaporating, thus creating partially-filled or empty pores which complicate the determination of pore size distribution. The encasing material for the porous rock sample is selected from film-forming polymeric materials which are impervious to the fluid or fluids in the porous rock sample. Such encasing materials can be applied to the porous rock samples as tightly fitting sleeves or as curable polymer formulations. Examples of such material include preformed tubes (sleeves) of polyethylene, poly(vinyl chloride), poly(tetrafluoroethylene), butadiene/styrene copolymer and the like, as well as, curable materials, such as epoxy resin, which can be applied as a semisolid thin film and cured to a tough impervious coating. It is not necessary that these encasing materials be proton-free, since the useful materials are solid in nature and do not produce spin echoes even though they do have protons. It is desirable that these films fit very tightly on the rock samples; films of liquid between the encasing material and the porous rock sample interfere with the spin echo measurements. It is within the scope of this invention, therefore, to use semisolid curable materials, such as epoxy resin, which penetrate the porous rock sample to a slight extent prior to curing and thus avoid the problem of liquid film between the rock surface and the encasing film. An alternative, and preferred method of encasing the rock sample employs a tube of suitable polymeric material which shrinks on contact with heat. The sample of rock is placed in the tube which is then exposed to heat which shrinks the polymeric material to form a tightly fitting sleeve around the rock sample.

This invention is generally useful with a wide variety of nonmagnetic porous rocks which are normally associated with natural formations which could be reservoirs for organic fluids, such as crude oil. Since ferromagnetic materials are known to interfere with nmr measurements, porous rocks useful in this invention will contain a maximum of about three percent by weight based on total porous rock and preferably will contain less than about one percent ferromagnetic material, such as iron.

Since porous rocks from reservoir formations frequently contain a mixture of water and organic material in the pores, it will generally be advisable to displace all of the mixture of fluids with a single fluid. Since brine (e.g., aqueous solution containing about 1200 ppm sodium chloride) inhibits the swelling of the naturally occurring clays in the reservoir core and since it responds to NMR techniques, brine is a preferred fluid for saturating the core samples and for displacing organic fluids.

In order to determine the size distribution of pores of a formation rock containing an organic fluid, the aqueous solution in a water and oil containing porous rock sample is displaced by flushing or pressurizing the sample with a "doped" brine solution followed by measurement as described above on the resultant sample. The organic components of the residual oil contain bound hydrogen and hence are sensitive to the above described NMR stimulated spin echo technique. "Doping" of the water solution with a transition metal salt is a well known method of eliminating the NMR response of the hydrogen in water. Thus, the rock samples containing oil and "doped" water will exhibit responses which are characteristic of only the organic material and the subsequent calculation will provide the pore size distribution of the oil containing pores. A knowledge of the pore size distribution of the total sample and a knowledge of the pore size distribution of the pores containing the residual oil aids in determining the composition of a fluid such as water with surfactant or a polar organic component which will displace the remaining oil.

The technique described in the preceding paragraph for determining the size distribution of pores of a formation rock containing an organic fluid is generally more useful with the crude oils of rather low viscosity. As the viscosity of the crude oil increases, the diffusion within the pores is restricted and the resultant stimulated spin echo signal will be of such an amplitude that measurement of the signal and subsequent calculations to obtain pore size distribution do not provide a realistic representation of the nature of the porous rock.

When pore size distribution of porous rock samples containing viscous crude oil is desired, the residual viscous oil is first stripped from the porous rock sample by methods known in the art which do not destroy nor alter the pore structure of the rock sample. The stripped rock sample is then saturated with a doped brine solution and then an organic fluid of lower viscosity than the original oil is passed into the sample to give a condition somewhat similar to the condition of the reservoir formation before removal of oil therefrom. Analysis of this "restored" porous rock by the above described stimulated spin echo technique provides the size distribution of the pores containing the organic material. Flushing of the "restored" porous rock with a doped brine solution in a manner analogous to secondary oil recovery techniques will give a sample containing water-filled pores and residual organic-filled pores in which the organic-filled pores are analogous to the oil-filled pores in the reservoir after water-flooding. Determination of the size distribution of the pores containing the residual organic fluid employing the above-described stimulated spin echo technique gives the approximate size distribution of the pores containing viscous crude oil in the water-flooded reservoir.

The organic fluids useful in this embodiment of the invention are generally selected from saturated aliphatic hydrocarbons containing from 6 to 12 and preferably 8 to 10 carbon atoms per molecule. Use of compounds with less than 6 carbon atoms is limited by their high volatility. Compounds with more than 12 carbon atoms generally have diffusion coefficients which are too small to be useful. Examples of useful compounds include n-hexane, n-octane, n-decane, n-undecane, iso-octane, neohexane and the like and mixtures of any two or more thereof.

The following example demonstrates the use of this invention in determining the pore size distribution in an actual reservoir sample.

EXAMPLE

The instrument employed in the measurement of pore size distribution was a custom-built, pulsed, single coil nuclear magnetic resonance spectrometer of conventional design capable of producing a 90° pulse in 5-6 microseconds and employing a 12 inch (30.5 cm) magnet (from Varian Associates, Palo Alto, California) with a 1.75 inch (4.4 cm) gap. The RF coil consisted of 6 to 7 turns of #14 enameled copper wire wound snugly around the sample container; the coil was tuned in a parallel circuit. The power supply connected to the gradient coils (Bruker Scientific, Inc., Palo Alto, California) was a current-regulated, D.C. power supply (Lambda Electronics Corp., Melville, Long Island, New York, Model LP-410A-FM). The current from the power supply was determined accurately by measuring the potential difference across a one ohm resistor.

The measurements were conducted at 30 megahertz (7,000 Gauss). A gradient range of 0.5 Gauss/cm to 6

Gauss/cm was employed in the measurement. The gradient was calibrated according to the procedure of Carr and Purcell, Phys. Rev. 94, 630 (1954). A custom-built, programmable, pulse delay unit was used to trigger the NMR transmitter and the data acquisition system.

The signal from the RF coil was amplified using a high impedance preamplifier of conventional design and a postamplifier (Model ITA-34-30-08-50 from Varian Associates, Palo Alto, California) and was amplitude detected using temperature compensated diodes and digitized by an analog-to-digital converter at a rate of 500 kiloHertz. The digitized data were accumulated in a computer (Model 2100 from Hewlett-Packard) over approximately 50 acquisitions to enhance the signal-to-noise ratio. The base line of the accumulated signal was subtracted from the total signal to give the spin echo amplitude the maximum value of which was determined by a least squares parabolic fit.

A sample of porous rock (13.5% porosity and 723 millidarcy permeability) from a reservoir fromation was obtained for testing. A cylinder of rock 1.25 cm diameter by 3.75 cm length was prepared by drilling. The outer curved surface of the cylinder was sealed by applying a sleeve of surface irradiated heat-shrinkable polyolefin tubing (Alpha Tubing Co.) and heating with a 1000 watt heat gun for about 1 minute. The heat-shrinkable tubing sealed glass tubing connections to the open ends of the enclosed rock cylinder. The rock sample was filled with sodium chloride brine (1200 ppm NaCl in water) by pressurizing at $1.7 \times 10^4$ kPa. In this state the sample is designated as being in the "preparative brine state".

Measurement of the spin echo amplitude of the sample in the preparative brine state and use of that amplitude to calculate mean, mode, median and standard deviation of the pore radii gave the values recorded in Table I. Pore size distribution was obtained by use of mean, mode, median and standard deviation of pore radii and is graphically represented in FIG. 7 which shows a plot of pore radius versus radius probability density function.

TABLE I

| Run No. | State | Mean ($\mu$m) | Mode ($\mu$m) | Median ($\mu$m) | Std. Dev. |
|---------|-------------|------|------|------|-----|
| 1 | Preparative | 18.5 | 14.0 | 16.8 | 8.4 |
| 2 | Restored | 6.1 | 1.4 | 3.7 | 8.0 |
| 3 | Residual | 6.4 | 2.0 | 4.3 | 7.0 |

The sample in the preparative brine state was then flushed with a brine solution (1200 ppm NaCl in water) also containing 0.001 M to 0.005 M $MnCl_2$ at 10 ft/day ($3.6 \times 10^{-3}$ cm/sec) flow rate. Th thus-flushed sample was then flushed with n-octane at $3.6 \times 10^{-3}$ cm/sec flow rate until about 75 volumes n-octane per pore volume in the rock sample was passed. In this state the sample is designated as being in the "restored" condition, which condition is believed to be analogous to the original reservoir formation prior to removal of crude oil therefrom. Measurement of the spin echo amplitude of the sample in the restored state and use of that amplitude to calculate mean, mode, median and standard deviation of the octane-filled pore radii gave the values recorded in Table I. Pore size distribution of octane-filled pores was obtained by use of the mean, mode, median and standard deviation and is graphically represented in FIG. 7.

The sample in the restored state was then flushed with the above-described brine solution containing 0.001 M–0.005 M $MnCl_2$ at $3.6 \times 10^{-3}$ cm/sec using 75 volumes of brine per pore volume or until no more octane was displaced. The sample in this state is designated as being in the "residual" state which is believed to be analogous to the original reservoir formation after secondary recovery attempts (water flooding) to remove crude oil. Measurement of the spin echo amplitude of the sample in the residual state and calculation of results as described above gave the mean, mode, median and standard deviation of octane-filled pores recorded in Table I and the pore size distribution recorded in FIG. 7.

As will be observed from Table I and FIG. 7, the pore size distribution of the preparation brine state was rather broad with a mean of 18.5 $\mu$m radius. When the sample was flushed with n-octane, the octane apparently displaced the brine in the smaller pores but not the larger pores since the mean of the restored state was 6.1 $\mu$m radius. In comparison of the restored state with the residual state, the slight shift to larger pore sizes for the octane-filled pores after brine flooding can be interpreted to mean that the octane in the smaller pores is displaced by the brine more readily than the octane in the larger pores.

It should be noted that the curves in FIG. 7 are normalized so that each contains the same area under the curve. Therefore no correlation between volume of octane and volume of brine is intended to be represented in FIG. 7.

Reasonable variations and modifications are possible within the scope of the disclosure and the appended claims to the invention.

That which is claimed is:

1. A method for determining the pore size distribution of a porous media comprising the steps of:
    (a) substantially saturating a sample of said porous media with a fluid which exhibits a response in a nuclear magnetic resonance spectrometer;
    (b) positioning the thus saturated sample in a static magnetic field $H_o$ and a magnetic field gradient G which is superpositioned on said static magnetic field $H_o$;
    (c) subjecting the thus positioned sample to a first radiofrequency pulse at a time $t_1$ to thereby rotate the precessing nuclear magnets associated with the fluid in said sample approximately 90° to generally the positive Y-axis of a reference frame which is rotating around the direction of the static magnetic field $H_o$ where the direction of the static magnetic field $H_o$ is the positive Z axis of said reference frame and the direction of the alternating magnetic field $H_1$ produced by said first radio frequency pulse is the positive X axis of said reference frame;
    (d) subjecting the thus treated sample to a second radio frequency pulse at a time $t_2$, which is later in time that said time $t_1$, to thereby rotate said precessing nuclear magnets approximately another 90° to generally the X-Z plane of said reference frame;
    (e) subjecting the thus treated sample to a third radiofrequency pulse at a time $t_3$, which is later in time than said time $t_2$, to thereby rotate said precessing nuclear magnets approximately another 90° to generally the X-Y plane of said reference frame;
    (f) measuring, by means of a nuclear magnetic spectrometer, the amplitude of the spin echo signal which occurs when the magnetization of said precessing nuclear magnets refocuses on generally the negative Y-axis of said reference frame after said time $t_3$;

(g) changing the magnetic field gradient G to a different magnitude;

(h) repeating steps c-g to obtain a plurality of spin echo amplitudes as a function of the magnitude of the magnetic field gradient G; and (i) determining the pore size distribution of said sample based on the plurality of spin echo amplitudes which are a function of the magnetic field gradient G.

2. A method in accordance with claim 1 wherein said fluid is brine.

3. A method in accordance with claim 1 wherein said reference frame is rotating at the Larmor frequency.

4. A method in accordance with claim 1 wherein the time period given by $t_2-t_1$ is sufficient to enable the nuclear magnetic resonance signal produced by said processing nuclear magnets to become unobservable on a nuclear magnetic resonance spectrometer.

5. A method in accordance with claim 4 wherein the time period $t_3-t_2$ is sufficiently long to allow appreciable diffusional interaction between the atoms of said fluid and the pore walls of said sample.

6. A method in accordance with claim 5 wherein said spin echo signal occurs at a period of time given by $t_2-t_1$ after said time $t_3$.

7. A method in accordance with claim 6 wherein said magnetic field gradient G is varied from about 0.5 Gauss/cm to about 6 Gauss/cm.

8. A method for determining the size distribution of pores in a sample of a porous medium which contains an aqueous solution and an organic fluid comprising the steps of:

(a) substantially displacing said aqueous solution with a third fluid which exhibits substantially no response in a nuclear magnetic resonance spectrometer;

(b) positioning the thus treated sample in a static magnetic field $H_o$ and a magnetic field gradient G which is superpositioned on said static magnetic field $H_o$;

(c) subjecting the thus positioned sample to a first radio frequency pulse at a time $t_1$ to thereby rotate the precessing nuclear magnets associated with the fluid in said sample approximately 90° to generally the positive Y-axis of a reference frame which is rotating around the direction of the static magnetic field $H_o$ where the direction of the static magnetic field $H_o$ is the positive Z axis of said reference frame and the direction of the alternating magnetic field $H_1$ produced by said first radio frequency pulse is the positive X axis of said reference frame;

(d) subjecting the thus treated sample to a second radio frequency pulse at a time $t_2$, which is later in time than said time $t_1$, to thereby rotate said precessing nuclear magnets approximately another 90° to generally the X-Z plane of said reference frame;

(e) subjecting the thus treated sample to a third radio frequency pulse at a time $t_3$, which is later in time than said time $t_2$, to thereby rotate said precessing nuclear magnets approximately another 90° to generally the X-Y plane of said reference frame;

(f) measuring, by means of a nuclear magnetic spectrometer, the amplitude of the spin echo signal which occurs when the magnetization of said precessing nuclear magnets refocuses on generally the negative Y-axis of said reference frame after said time $t_3$;

(g) changing the magnetic field gradient G to a different magnitude;

(h) repeating steps c-g to obtain a plurality of spin echo amplitudes as a function of the magnetic field gradient G; and (i) determining the pore size distribution of the pores of said sample which contain said organic fluid based on the plurality of spin echo amplitudes which are a function of the magnitude of the magnetic field gradient G.

9. A method in accordance with claim 8 wherein said third fluid is brine containing a transition metal salt.

10. A method in accordance with claim 8 wherein said reference frame is rotating at the Larmor frequency.

11. A method in accordance with claim 8 wherein the time period given by $t_2-t_1$ is sufficient to enable the nuclear magnetic resonance signal produced by said precessing nuclear magnets to become unobservable on a nuclear magnetic resonance spectrometer.

12. A method in accordance with claim 11 wherein the time period $t_3-t_2$ is sufficiently long to allow appreciable diffusional interaction between the atoms of said organic fluid and the pore walls.

13. A method in accordance with claim 12 wherein said spin echo signal occurs at a period of time given by $t_2-t_1$ after said time $t_3$.

14. A method in accordance with claim 13 wherein said magnetic field gradient G is varied from about 0.5 Gauss/cm to about 6 Gauss/cm.

15. A method for determining the size distribution of pores of a porous medium which contain a viscous organic fluid comprising the steps of:

(a) stripping said viscous organic fluid from a sample of said porous media;

(b) substantially saturating the thus stripped sample of said porous media with a substitute fluid which exhibits substantially no response in a nuclear magnetic resonance spectrometer;

(c) introducing a second organic fluid having a lower viscosity than said viscous organic fluid into the saturated sample to thereby displace at least a portion of said substitute fluid to thereby produce a restored porous media;

(d) flushing said restored porous media with said substitute fluid;

(e) positioning the thus flushed restored porous media in a static magnetic field $H_o$ and a magnetic field gradient G which is superpositioned on said static magnetic field $H_o$;

(f) subjecting the thus positioned flushed restored porous media to a first radio frequency pulse at a time $t_1$ to thereby rotate the precessing nuclear magnets associated with the fluid in said flushed restored porous media approximately 90° to generally the positive Y-axis of a reference frame which is rotating around the direction of the static magnetic field $H_o$ where the direction of the static magnetic field $H_o$ is the positive Z axis of said reference frame and the direction of the alternating magnetic field $H_1$ produced by said first radio frequency pulse is the positive X axis of said reference frame;

(g) subjecting the thus treated flushed restored porous media to a second radio frequency pulse at a time $t_2$, which is later in time than said time $t_1$, to thereby rotate said precessing nuclear magnets approximately another 90° to generally the X-Z plane of said reference frame;

(h) subjecting the thus treated flushed restored porous media to a third radio frequency pulse at a time $t_3$, which is later in time than said time $t_2$, to thereby rotate said precessing nuclear magnets approximately another 90° to generally the X-Y plane of said reference frame;

(i) measuring, by means of a nuclear magnetic spectrometer, the amplitude of the spin echo signal which occurs when the magnetization of said precessing nuclear magnets refocuses on generally the negative Y-axis of said reference frame after said time $t_3$;

(j) changing the magnetic field gradient G to a different magnitude;

(k) repeating steps f–j to obtain a plurality of spin echo amplitudes as a function of the magnitude of the magnetic field gradient G; and (l) determining the pore size distribution of the pores of said sample which contain said viscous organic fluid based on the plurality of spin echo amplitudes which are a function of the magnitude of the magnetic field gradient G.

16. A method in accordance with claim 15 wherein said substitute fluid is brine containing a transition metal salt.

17. A method in accordance with claim 15 wherein said reference frame is rotating at the Larmor frequency.

18. A method in accordance with claim 15 wherein the time period given by $t_2 - t_1$ is sufficient to enable the nuclear magnetic resonance signal produced by said precessing nuclear magnets to become unobservable on a nuclear magnetic resonance spectrometer.

19. A method in accordance with claim 18 wherein the time period $t_3 - t_2$ is sufficiently long to allow appreciable diffusional interaction between the atoms of said second organic fluid and the pore walls.

20. A method in accordance with claim 19 wherein said spin echo signal occurs a period of time given by $t_2 - t_1$ after said time $t_3$.

21. A method in accordance with claim 20 wherein said magnetic field gradient G is varied from about 0.5 Gauss/cm to about 6 Gauss/cm.

* * * * *